United States Patent [19]
Ward et al.

[11] Patent Number: 6,030,789
[45] Date of Patent: Feb. 29, 2000

[54] HUMAN CONJUNCTIVAL EPITHELIAL CELL LINES WITH AN EXTENDED LIFE SPAN

[75] Inventors: Sherry L. Ward, Montgomery Village, Md.; Tracey L. Walker, Woodbridge, Va.

[73] Assignee: The Gillette Company, Boston, Mass.

[21] Appl. No.: 09/265,386

[22] Filed: Mar. 10, 1999

[51] Int. Cl.$^7$ .................................................. C12Q 1/68
[52] U.S. Cl. ............................ 435/6; 435/467; 435/371
[58] Field of Search ............................... 435/371, 6, 440, 435/467

[56] References Cited

U.S. PATENT DOCUMENTS

| | | | |
|---|---|---|---|
| 4,760,020 | 7/1988 | Neufeld et al. | 435/29 |
| 4,835,102 | 5/1989 | Bell et al. | 435/29 |
| 5,374,515 | 12/1994 | Parenteau et al. | 435/1.1 |
| 5,585,265 | 12/1996 | Kahn et al. | 435/6 |
| 5,602,028 | 2/1997 | Minchinton | 435/401 |
| 5,672,498 | 9/1997 | Walker et al. | 435/371 |
| 5,766,875 | 6/1998 | Hafeman et al. | 435/29 |
| 5,786,201 | 7/1998 | Kahn et al. | 435/325 |

OTHER PUBLICATIONS

S. Green et al., "Criteria for In vitro Alternatives for the Eye Irritation Test" Fd Chem. Toxic, vol. 31, No. 2, pp. 81–85, (1993).
R. Curren et al., "In Vitro Alternatives for ocular irritation", Environmental Health Perspectives, vol. 106, Supplement 2, pp. 485–491 (Apr. 1998).
F. Kruszewski, "Human Cells as In Vitro Alternatives for Ocular Toxicity Studies", Comments Toxicology, vol. 6, No. 3, pp. 221–233 (1998).
R. Roguet et al., "An Interlaboratory Study of the Reproducibility and Relevance of Episkin, a Reconstructed Human Epidermis, in the Assessment of Cosmetics Irritancy", Toxicology in Vitro vol. 12, pp. 295–304 (1998).
R. Shih–Man Chang "Continuous Subcultivation of Epithelial–like Cells from Normal Human tissues", Proc Soc Exp Biol Med vol. 87, pp. 440–43 (1959).
Sam C. Wong et al., "Changing Viral Susceptibility of a Human Cell line in Continuous Cultivation", J. Exp. Med. vol. 113, pp. 95–110 (1961).
A.J. Bron et al., "The Normal Conjunctival and its Response to Inflammation", Trans Ophthalmol. Soc. U.K., vol. 104, pp. 424–435 (1985).
C. Kahn, "Human Corneal Epithelial Primary Cultures and Cell Lines With Extended Life Span: In Vitro Model for Ocular Studies" Investigative ophthalmology & Visual Science, vol. 43, No. 12, pp. 3429–3441 (Nov. 1993).
Y. Diebold, "Characterization of Epithelial Primary Cultures From Human Conjunctiva", Graefe's Arch Clin Exp Ophthalmol pp. 268–276 (1997).
A. Niiya et al ., "Collagen gel–embedding Culture of Conjunctival Epithelial Cells", Graefe's Arch Clin Exp Ophthalmol, pp. 32–40 (1997).

K. Lindberg et al., "In Vitro Propagation of Human Ocular Surface Epithelial Cells for Transplantation", Investigative Ophthalmology & Visual Science vol. 34, No. 9, pp. 2672–2679 (Aug. 1993).
P. Saha, "A Primary Culture Model of Rabbit Conjunctival Epithelial Cells Exhibiting Tight Barrier Properties", Current Eye Research, pp. 1163–1169 (1996).
P. Saha, "Permeability Characteristics of Primary Cultured Rabbit Conjunctival Epithelial Cells to Low Molecular Weight Drugs", Current Eye Research, pp. 1170–1174 (1996).
L. Li et al., "Eye Tissues Grown in 3–Dimensional Histoculture for Toxicological Studies", J. Cell Pharmacol, vol. 2, pp. 311–316 (1991).
Ray Jui–Fang Tsai et al., "The Effects of Fibroblasts on the Growth and differentiation of Human Bulbar Conjunctival Epithelial Cells in an In Vitro Conjunctival Equivalent", Investigative Ophthalmology& Visual Science, vol. 35, No. 6, pp. 2865–2875 (1994).
J.L. Ubels et al., "Retinoic Acid Decreases the Number of EGF Receptors in Corneal Epithelium and Chang Conjunctival Cells", Exp. Eye Res. vol. 52, pp. 763–765 (1991).
Nobuo Takahashi, "A New Method Evaluating Quantitative Time–Dependent Cytotoxicity of Ophthalmic Solutions in Cell Culture. Beta–adrenergic blocking agents", Graefe's Arch Clin Exp Ophthalmol, vol. 220, pp. 264–267 (1983).
F.H. Kruszewski et al., "Evaluation of a Human Corneal Epithelial Cell Line as an in Vitro Model for Assessing Ocular Irritation", Fundamental and Applied Toxicology, vol. 36, pp. 130–140 (1997).
Simon L. Cassidy et al., "In Vitro Eye Irritation Studies on Organosilicon Compounds", J. Toxicol.—Cut. & Ocular Toxicol., vol. 16(l), pp. 45–60 (1997).
Zieski et al., "Basement Membrane Assembly and Differentiation of Cultured Corneal Cells: Importance of Culture Environment and Endothelial Cell Interaction", Exp Cell Res, vol. 214(2), pp. 621–33 (Oct. 1994) Abstract only.
T. Donnelly et al., "A Three–Dimensional In Vitro Model for the Study of Ocular Cytotoxicity and Irritancy", Toxic. in Vitro, vol. 8, No. 4, pp. 631–633 (1994).

(List continued on next page.)

Primary Examiner—James Ketter
Attorney, Agent, or Firm—Burns, Doane, Swecker & Mathis, L.L.P.

[57] ABSTRACT

The present invention provides two human conjunctival epithelial cell lines with an extended life span, designated HC0597 and HC0708, and methods for producing such cell lines. These conjunctival cell lines can be cultured as stratified 3-dimensional (3-D) cultures. In turn, the 3-D cultures can be used as tissue- and species-specific cellular models of the human conjunctival ocular surface. These human conjunctival cultures are particularly useful, for example, in product safety evaluations to test products for their eye irritation potential.

9 Claims, 8 Drawing Sheets

OTHER PUBLICATIONS

R. Osborne et al., "Development and Intralaboratory Evaluation of an in Vitro Human Cell–Based Test to Aid Ocular Irritancy Assessments", *Fundamental and Applied Toxicology*, vol. 28, pp. 139–153 (1995).

Murayama et al. "Cytotoxicity and Characteristics of Mitomycin" *C. Ophthalmic Res.*, vol. 28, pp. 153–159 (1996).

Takahashi et al. "A Flow Cytometric Study of the Effects of Benzalkonium Chloride on the Cell Cycle", *Nippon Ganka Gakkai Zasshi*, vol. 96, pp. 823–827 (1992).

Symposium Proceedings, "Replacing the Draize Eye Irritation Test: Scientific Background and Research Needs", *J. Toxicol.—Cut.& Ocular Toxicol.*vol. 15, No. 3, pp. 211–234 (1996).

Ward et al., "Tight Epithelial Barrier Established by Transfected Human Conjunctival Cell Lines", B320, IOVS, Mar. 15, 1998, vol. 39, No. 4.

Kulkarni et al., "Characterization of Human Buccal Epithelial Cells Transfected with the Simian Virus 40 T–antigen Gene", *Carcinogenesis* 16(10):2515–2521 (1995).

Reddel et al., "SV40–Induced Immortalization and Ras–Transformation of Human Bronchial Epithelial Cells", *Int J Cancer* 61(2):199–205 (1995).

Merviel et al., "Normal Human Endometrial Cells in Culture: Characterization and Immortalization of epithelial and Stromal Cells by SV 40 Large T Antigen ", *Biol Cell* 84(3):187–193 (1995).

Jiang et al., "Comparison of Methods for Transfection of Human Epidermal Keratinocytes", *J Invest Dermatol* 97 (6):969–973 (1991).

Lechner et al., "Human Epithelial Cells Immortalized by SV40 Retain Differentiation Capabilities in an In vitro Raft System and Maintain Viral DNA Extrachromosomally", *Virology* 195(2):563–571 (1991).

Delarue et al., "Stable Cell Line of T–SV40 Immortalized Human Glomerular Visceral Epithelial Cells", *Kidney Int* 40(5):906–912 (1991).

Inokuchi et al., "Immortalization of Human Epidermal Keratinocytes by the Recombinant SV40 Adenovirus Vector", *In Vitro Cell Dev Biol.*, 27A(11):827–828 (1991).

Stoner et al., "Establishment and Characterization of SV40 T–Antigen Immortalized Human Esophageal Epithelial Cells", *Cancer Res* 15(1):365–371 (1991).

Dutt et al, "Establishment of Human Retinal Pigment Epithelial Cell Lines by Oncogenes", *Oncogene* 5(2):195–200 (1990).

Morphology was not altered by transfection.

Fig. 1A 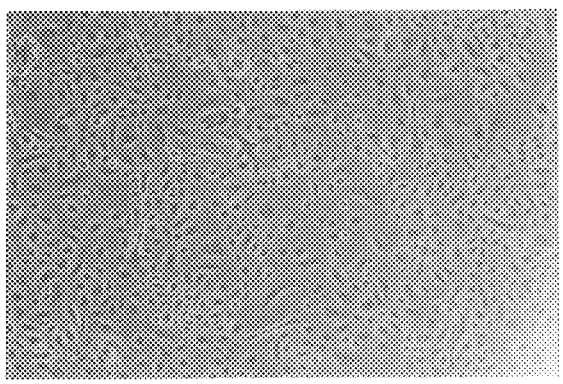 Fig. 1B 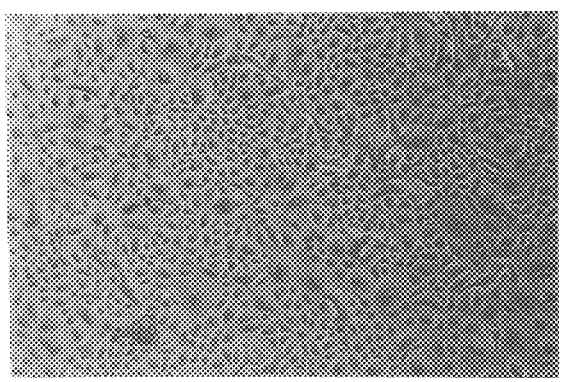

Primary conjunctival cells used to produce cell line HC0597; passage #3 (63 x).

Transfected conjunctival cell line HC0597; passage #3 (63 x).

Human bulbar conjunctival epithelial cells were transfected with the large T antigen plasmid, pRSV-T, during passage #2. The primary cultures senesced at passage #8, while the transfected cultures continued until passage #30 before the growth slowed significantly.

Fig. 2A
Fig. 2B
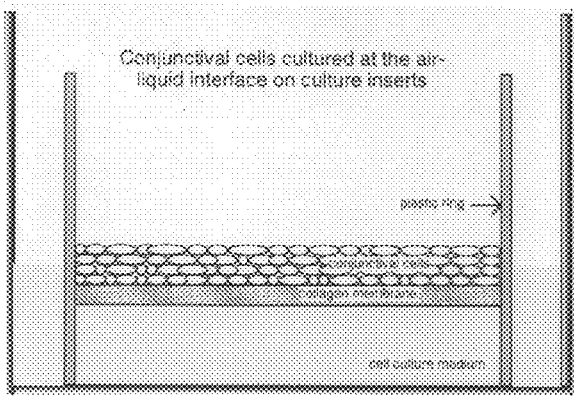
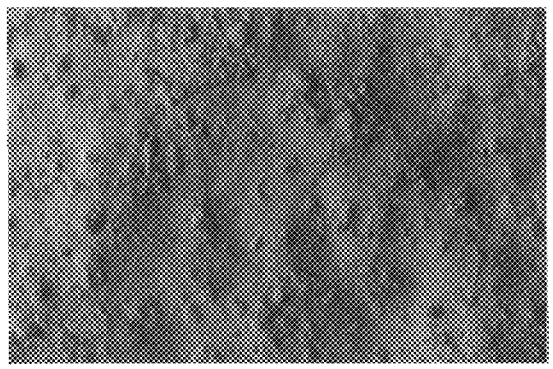
Both conjunctival cell lines form stratified cultures when grown on permeable membranes in serum-free KGM. The photomicrograph shows the appearance of the air-exposed, apical surface of a stratified culture of HC0597 at passage #20 as visualized by light microscopy (63 x).

Keratin 4 Reactivity with HC0597 (P13)
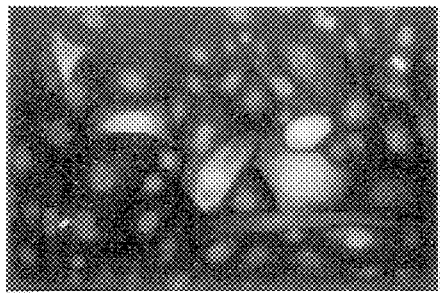 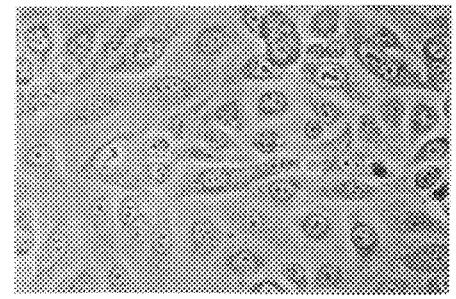
 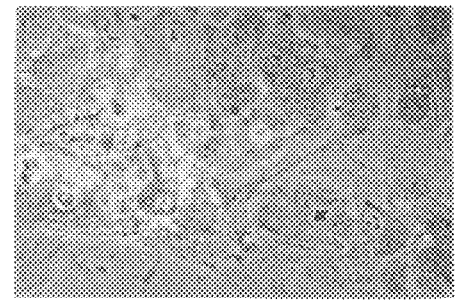
0.15 mM calcium
1.65 mM calcium
250x            320x
Fig. 3

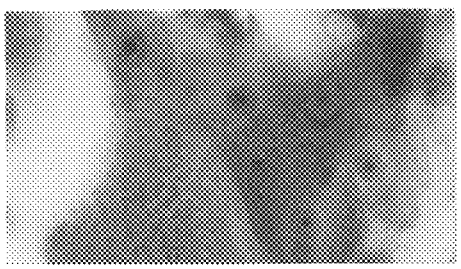
Fig. 5A1
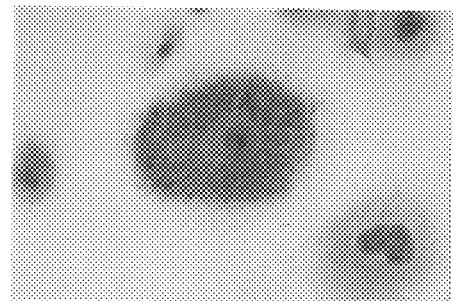
Fig. 5A2
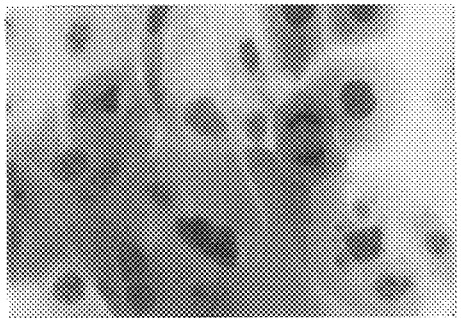
Fig. 5A3
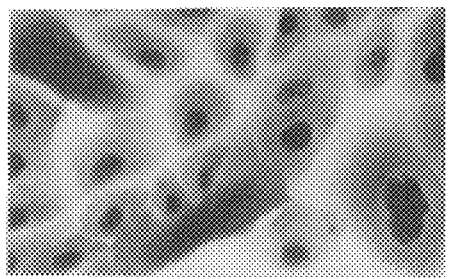
Fig. 5A4

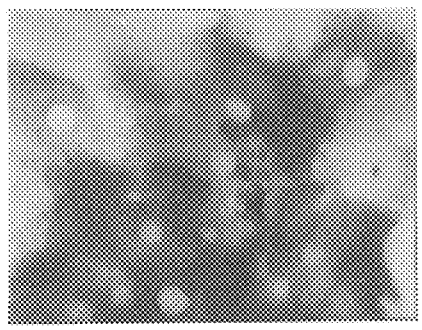
Fig. 5B1
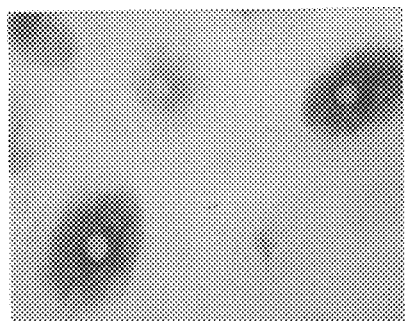
Fig. 5B2
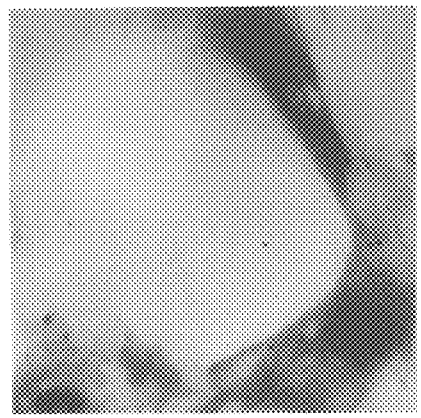
Fig. 5B3
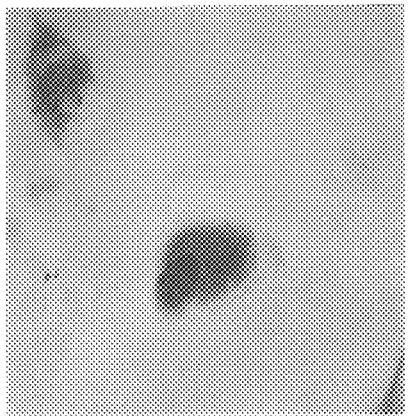
Fig. 5B4

HUMAN CONJUNCTIVAL EPITHELIAL CELL LINES WITH AN EXTENDED LIFE SPAN

BACKGROUND OF THE INVENTION

1. Field of the Invention

The present invention provides human conjunctival epithelial cell lines with an extended life span. These conjunctival cell lines can be cultured as stratified 3-dimensional (3-D) cultures. The 3-D cultures can be used as tissue- and species-specific cellular models of the human conjunctival ocular surface. These human conjunctival cultures are particularly useful in product safety evaluations to test products for their eye irritation potential.

2. Description of the Related Art

Injury to the eye from exposure to chemicals can result in blindness. Accordingly, to protect against inadvertent damage from commercially applied materials, the Food, Drug, and Cosmetic Act of 1938 has required testing of cosmetic and drug products.

Prior to the present invention, the most common method for testing ocular irritancy in humans employed rabbits. The test, known as the "Draize Test," involves placing the foreign substance to be tested directly into the conjunctival sac of the rabbit eye. The Draize Test was first described in Draize et al (1944) *J. Pharm. Exp. Ther.* 83:377–390. The Draize Test is simple to perform, provides quick, economical results, and uses a laboratory animal which is easy to breed and maintain. The conjunctiva and cornea provide different components of the overall biological response of the ocular surface, and in particular the cornea and conjunctiva, to noxious compounds.

The corneal epithelium is a transparent barrier that also aids in maintaining the transparency of the underlying corneal stroma. The transparency allows light penetration to the retina and is crucial to visual acuity. The corneal response in the Draize test is assessed by the degree of damage to the corneal epithelium, and the degree of corneal opacity, resulting from contact with the test substance. The cornea is highly innervated to within several microns of the ocular surface, and thus provides a significant part of the neural response (burning, stinging, etc.) to eye irritants.

The conjunctiva is the tissue that lines the eyelids, and covers the anterior portion of the globe of the eye (except for the cornea). The conjunctiva consists of a delicate membrane composed of an epithelium, and a substantia propria, that overlie the tough outer portion of the eyeball known as the sclera. The epithelium is stratified into multiple cell layers, and provides a barrier to the penetration of compounds into the eye. There are desmosomal junctions connecting the epithelial cells to one another, and tight junctions between the surface cells that prevent the penetration of small ions. Other cells that can be found in the normal conjunctival epithelium include: goblet cells, which are specialized cells that secrete mucin; Langerhans cells; melanocytes; a small population of immune cells (lymphocytes and neutrophils); and an interspersed neuronal component. Beneath the epithelium, the substantia propria contains stromal cells interspersed in a layer of connective tissue. The substantia propria also contains a microvasculature, lymphatics, immune cells, and neurons. Mast cells are not found in the normal conjunctival epithelium, but tissue type mast cells reside in the substantia propria. The conjunctiva responds to eye irritants by mounting an inflammatory response. The conjunctival response is assessed in the Draize rabbit eye test as redness, chemosis, and discharge.

However, there are drawbacks to the Draize Test, including the morphological differences between the rabbit eye and the human eye, overprediction of the Draize test, variability from animal to animal and from lab to lab, and the adamant opposition of animal rights activists to the use of animals in such tests.

In vitro models for human corneal epithelium have been developed, including those described in U.S. Pat. No. 5,672,498, U.S. Pat. No. 5,786,201, and U.S. Pat. No. 5,585,265, the contents of all of which are hereby incorporated by reference. However, toxicologists, regulatory agency scientists and ophthalmologists have questioned the validity of extrapolating results from an in vitro model that represented only corneal effects to the Draize test, which represents corneal (73%), conjunctival (18%), and iridial (9%) responses. The conjunctival response to noxious compounds has been identified as an important element of the human ocular response, and as independent of the corneal response for at least some compounds. Indeed, it has been noted that ocular exposures (Draize tests) to some products resulted in an adverse reaction in only the conjunctiva of the rabbit. Examples have also been reported in the literature where conjunctival signs were the only clinical response to an ocular exposure.

It is, therefore, thought that combined conjunctival and corneal response data will provide information more likely to be representative of the overall human ocular response from exposure to a noxious compound. Multiple tests that measure different mechanisms of injury in the two tissues provide a composite test battery that can serve as a replacement for the Draize test. With this type of test system, compounds that elicit primarily a conjunctival response will not be "missed" by testing on only a corneal model, thereby providing a more effective in vitro test scheme.

However, prior to the present invention, it has been extremely difficult to assess conjunctival response to exposure to noxious substances in vitro. There are no reports of transfected conjunctival cell lines, either human or animal, in the scientific literature. The only conjunctival cell line available from the American Type Culture Collection (ATCC) is the Chang cell line. Accordingly, investigators wishing to study the human conjunctiva must do clinical studies, or use primary conjunctival tissue or cell cultures. For in vitro studies three possible sources of conjunctival cells exist: (1) the Chang cell line; (2) primary human conjunctival cell cultures; and (3) primary human conjunctival tissue specimens.

The Chang conjunctival cell line is described to be of human conjunctival origin (Chang, 1954; Wong & Kilbourne, 1961). The Wong-Kilbourne derivative of Chang conjunctiva is available from the ATCC (ATCC CCL 20.2.; ATCC Catalog, 7th ed., 1992). There are two principal problems with using Chang cells. First, Chang cell cultures do not retain many of the characteristics of the conjunctival epithelium. No publication has been found that compares the characteristics of Chang cells and primary conjunctival epithelial cells. Most authors note that data obtained using the Chang cell line should be interpreted with caution. Reports citing the use of the Chang cell line are frequently for viral propagation studies, since it is not commonly used for studies on conjunctival biology. Second, the Chang cell line from the ATCC is reported to contain HeLa cell marker chromosomes. ATCC recommends that "such lines should not be chosen for study when the specific organ or tissue of presumptive origin is of importance to the validity of the research."

Many investigators use primary cultures of human conjunctival epithelial cells. Primary cells are most often cultured as monolayers, but have been cultured stratified on permeable membranes. Problems with using primary conjunctival cells include limited availability, biological variability, difficulty in establishing the cultures, potential contamination with infectious agents, finite life spans, and multiple cell types. Primary conjunctival cells and tissues are typically obtained from surgery specimens, limiting the amount available. Conjunctival tissue is highly vascularized, and degrades rapidly after donor death. It must be harvested within 15 hours, and preferably within 8 hours postmortem. Many eye banks cannot accommodate this type of tissue collection schedule, which highly limits access to fresh conjunctival tissue. Most investigators that use fresh conjunctival tissue are professionally associated with an eye bank. Conjunctival tissue can also be isolated and used as pieces of tissue, or maintained as an organ cultured tissue. However, the use of such tissue cultures presents the same problems as the use of primary cultures.

Other in vitro models that have been used for the evaluation of eye irritation include: monolayer cultures of animal or human ocular cells (cornea or conjunctival), or skin cells; monolayer cultures of MDCK cells on porous membranes (dog kidney epithelial cell line); multilayered cultures composed of human skin cells; a variety of other non-species and non-tissue specific in vitro models, including EYTEX, CAM, CAMVA, HET-CAM; multilayered cultures of primary, non-human ocular cells; and multilayered cultures of primary, human ocular cells. Problems with these in vitro models include:

1) The limited, or lack of, biological relevance to the tissue of the ocular surface. Monolayer cultures do not form the same barrier to toxic compounds that is found at the in vivo ocular surface. Monolayer cultures are more susceptible to chemical injury and do not recover as well as stratified tissue constructs (Ward, 1997). Non-human and non-ocular cell types are not biologically relevant for the assessment of human eye irritation.

2) Appropriate endpoints of toxicity and irritation for the conjunctival ocular surface have not been determined. Non-ocular and non-human cells may not be useful for this determination. Monolayer cultures do not provide an adequate response that is translatable to the human ocular surface response to injury/irritation.

Therefore, in view of the aforementioned deficiencies attendant with prior art methods of evaluating the eye irritation potential of consumer products in vitro, it should be apparent that there still exists a need in the art for a continuous conjunctival epithelial cell line.

SUMMARY OF THE INVENTION

Briefly, the present invention provides in vitro test methods that replace the Draize rabbit eye test for the evaluation of the eye irritation potential of products. In particular, the present invention provides transfected human conjunctival epithelial cell line(s), and methods of producing and characterizing such cell lines.

In a further embodiment, the present invention provides an in vitro model of the conjunctival portion of the human ocular surface comprising the cell lines of the present invention. This model can be used to evaluate the conjunctival component of the eye irritation potential of consumer products. This model can be used alone, or to complement testing on human corneal epithelial cells, as part of a test battery that could serve as a replacement for the Draize test for the evaluation of the eye irritation potential of some types of products.

The present invention also provides in vitro test methods that are predictive of the human ocular response to eye irritants, thereby, providing an additional in vitro test method for toxicologists to use in product safety evaluations.

A major objective of the invention is to provide human conjunctival epithelial cell lines with an extended life span. The cell lines can be maintained in culture for an increased period as continuous stable cell lines. The cells retain morphological characteristics similar to primary cells from which they were derived. The cells also retain phenotypic traits of human conjunctival epithelial cells.

Another objective of the invention is to provide an in vitro model of the human conjunctival surface. The cell lines with extended life span can be grown as stratified cultures to model in vivo human conjunctiva, providing a system with the potential to determine the effect of a chemical or drug on the conjunctiva of the eye.

The cell lines of the present invention may advantageously be used for toxicological testing; product safety evaluations; research on pathophysiologic mechanisms of anterior ocular surface injury and eye irritation from chemical and consumer product exposures; contact lens research (including product safety, product efficacy, and product development); ophthalmologic drug research (including efficacy, penetration, and safety evaluations); ocular penetration testing; gene therapy (safety, efficacy, and methods development); to provide conjunctival tissue for transplantation; in research on surgical procedures and wound healing; and in research on pathophysiologic mechanisms of anterior ocular surface disease and injury.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIGS. 1A and 1B illustrate morphology of primary and transfected conjunctival cells. FIG. 1A: primary conjunctival cells used to produce cell line HC0597; passage #3 (P3)(63×). FIG. 1B: transfected conjunctival cell line HC0597; passage #3 (63×).

FIG. 2A is a diagrammatic representation of how conjunctival cell lines form stratified cultures when grown on permeable membranes in serum-free KGM. FIG. 2B shows the appearance of the air-exposed, apical surface of a stratified culture of HC0597 at passage #20 as visualized by light microscopy (63×).

FIG. 3 Anti-K4 reacted with individual cells (top left panel) when HC0597 cells were cultured in low-calcium KGM. Anti-K4 reacted with large sheets of cells (bottom left panel) when the HC0597 cells were cultured in high-calcium KGM. Phase photomicrographs show how the cells grow as a monolayer in low-calcium KGM (upper right panel), and how they grow on top of each other in high-calcium KGM (lower right panel).

FIGS. 5A1–5A4 (PAS-hematoxylin) show photomicrographs of monolayer cultures stained with PAS-hematoxylin to detect the presence of goblet cells. The bright pink/magenta stained cells show positive staining. FIG. 5A1: Cell line HC0597 (P5), 0.15 mM calcium; FIG. 5A2: HC0597

(P5), 1.65 mM calcium; FIG. 5A3: Cell line HC0708 (P5), 0.15 mM calcium; FIG. 5A4: HC0708 (P5), 1.65 mM calcium. FIGS. 5B1–5B4 (alcian blue-PAS) show photomicrographs of monolayer cultures stained with alcian blue-PAS to detect the presence of goblet cells. The bright pink/magenta stained cells show positive staining. FIG. 5B1: Cell line HC0597 (P5), 0.15 mM calcium; FIG. 5B2: HC0597 (P5), 1.65 mM calcium; FIG. 5B3: Cell line HC0708 (P %), 0.15 mM calcium; FIG. 5B4: HC0708 (P5), 1.65 mM calcium. Magnification is 250× for all photos.

FIG. 6A: 7250×; FIG. 6B: 4751×.

DETAILED DESCRIPTION OF THE PREFERRED EMBODIMENTS OF THE INVENTION

Figure 4:
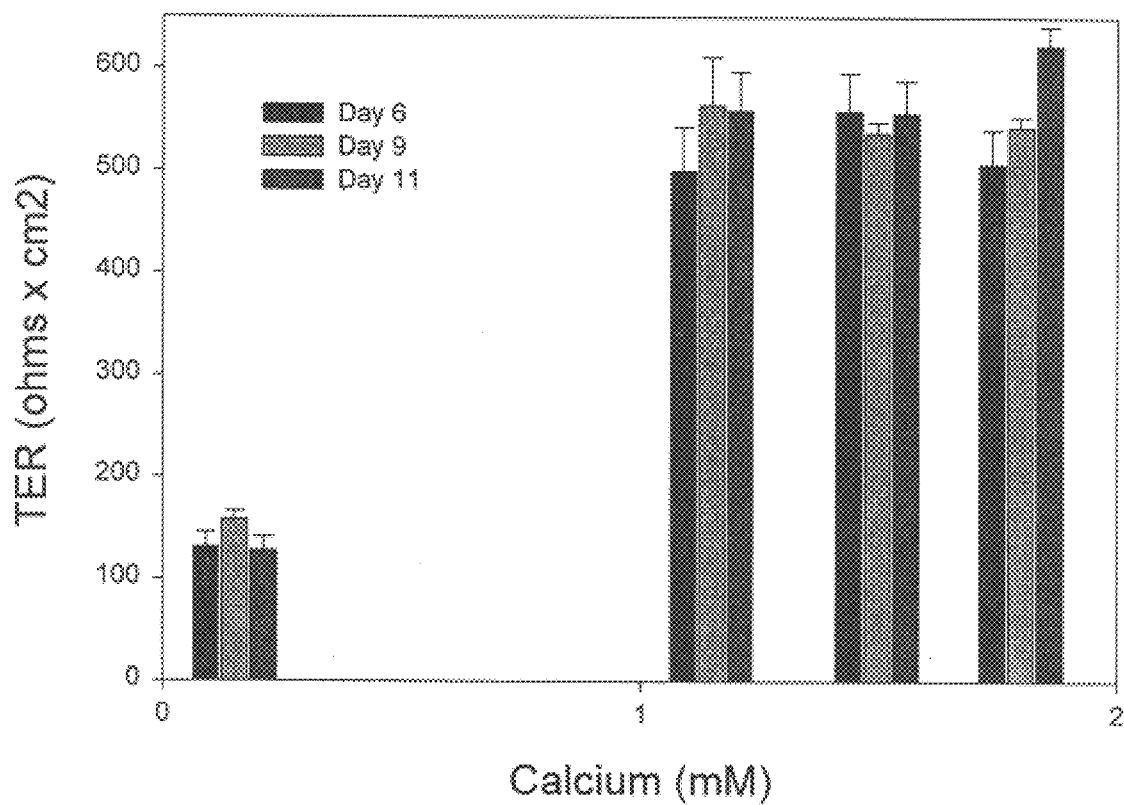
FIG. 4. The effect on transcepithelial electrical resistance (TER;Ω×cm$^2$) of maintaining HC0597 cells in media (KGM) containing different concentrations of calcium (mM) for cell line HC0597; data measured on days 6, 9 and 11.

The present invention provides in vitro test methods that replace the Draize rabbit eye test for the evaluation of the eye irritation potential of products. The Draize test provides data from three different ocular tissues—the cornea, the conjunctiva, and the iris—over time. A human conjunctival ocular model complements existing human corneal epithelial cell models by providing an in vitro model of a second tissue that is evaluated in the Draize eye test. In order to replace the Draize test with in vitro test methods, a test battery composed of multiple test methods from one, two, or three of these ocular tissues would be preferable. In addition, a method is needed to assess the "recovery" of the in vitro tissue(s) from the initial insult. The 3-D conjunctival model can be maintained for at least two weeks in culture, allowing the development of assays to evaluate recovery.

The human conjunctival epithelial cell lines of the present invention are species and tissue specific, providing biological relevance for test methods that may be developed using the cell lines or the 3-D conjunctival model. The cell lines retain morphological and phenotypic similarity to the tissue of origin, providing confidence in their biological relevance. The 3-D model provides a tissue that is ultrastructurally and functionally similar to the in vivo tissue, providing a useful and biologically relevant in vitro model for its proposed uses. Test battery data from this kind of biologically relevant human ocular model enables a more accurate prediction of the ocular irritation potential of consumer products than other currently available in vitro test methods.

In particular, the present invention provides human conjunctival epithelial cell lines with an extended life span. The cell lines can be maintained in culture for an increased period as continuous stable cell lines. The cells retain morphological characteristics similar to primary cells from which they were derived. The cells also retain phenotypic traits of human conjunctival epithelial cells, including:

1. epithelial cell morphology—shown by light microscopy photomicrographs of monolayer cultures;
2. conjunctive epithelial ultrastructural features—expressed in stratified cultures shown in transmission electron microscopy (TEM) photomicrographs;
3. epithelial cell specific expression of keratin proteins—shown by immunofluorescent localization using keratin antibodies and microscopy;
4. differentiation induced by high-calcium medium—shown by changes in cell morphology in different concentrations of calcium, and by increased expression of tight junctions and the related transepithelial electrical resistance (TER), a differentiation-related function;
5. expression of the keratin K4 in differentiated conjunctival cells AND modulation of differentiation by physiologically relevant stimuli—shown by immunofluorescent localization using keratin antibodies and microscopy—conjunctival cultures maintained under conditions that induce differentiation (high calcium media) contain more cells that express K4, while conjunctival cultures maintained under conditions that inhibit differentiation (e.g., inclusion of retinoic acid or retinol in media) contain fewer cells that express K4;
6. expression of tight junctions by cultures maintained on permeable membranes—shown by measurement of a TER across the cultures, and by visualization of tight junctional complexes by TEM;
7. expression of the mucin MUC5ac;
8. expression of goblet cells in monolayer cultures of the cell lines—shown by immunofluorescence staining of goblet cells with an antibody to keratin 7 and histochemical staining (PAS);
9. expression of inflammatory mediators characteristic of conjunctival epithelial cells—shown by ELISA—the cell lines express small amounts of IL-1$\alpha$, IL-ra, IL-8, IL-6 and GM-CSF;
10. expression of inflammatory mediators (RANTES) in response to specific pathophysiologically relevant mediators (MBP and EPO); and
11. expression of the conjunctival epithelial adhesion molecule ICAM-1—shown by ELISA.

Cells useful for the present invention can be derived from any human donor conjunctiva, regardless of age. Preferably, donor conjunctiva have been determined to be uninfected by any virus, especially hepatitis B, hepatitis C, or human immunodeficiency virus (HIV).

Cells may be derived from the conjunctiva by any method known in the art. In a preferred embodiment, conjunctiva are derived from surgery specimens according to the following method. Tissue specimens are transported to the lab in sterile culture media on ice. The tissues are transferred to a 15 ml centrifuge tube, and incubated overnight at room temperature in media containing trypsin-pronase. The next day the tissue is vortexed repeatedly to detach the epithelial cells. Remaining pieces of connective tissue are preferably removed from the solution, e.g. with sterile forceps, and the epithelial cells are collected by centrifugation. The cell pellet is resuspended in fresh, serum-free KGM, and the cells are seeded onto a FNC-coated T-25 flask. The cells are preferably cultured for about a week prior to shipment.

Transfections will preferably be performed using the same procedure used to produce human corneal cell lines described in U.S. Pat. Nos. 5,672,498 and 5,786,201, the contents of which are incorporated herein by reference. This procedure uses the large T antigen plasmid RSV-T. Specifically, the method for producing an immortalized human conjunctival epithelial cell line according to the present invention comprises: (a) culturing human conjunctival epithelial cells in serum-free medium; (b) transfecting said cells with a vector capable of transfecting said conjunctival epithelial cells such that said cells become continuously growing; (c) recovering said continuously growing conjunctival epithelial cells; and (d) retention of cell lines that retain their phenotypic characteristics, including stratification and transepithelial barrier function. In a preferred embodiment, the vector is a large T antigen plasmid, preferably pRSV-T.

Cell lines according to the present invention have an extended life span, allowing the development of reproducible cell models and test methods. The cell lines can be frozen for long-term storage and transportation, providing for the maintenance and transfer of the technology.

The new conjunctival cell lines retain many of the characteristics of primary conjunctival cell cultures, including: morphology on plastic; growth rate; types of keratins expressed (including, for example, keratin 4); expression of adhesion molecules (e.g., ICAM-1) expression of mucin (including MUC5ac); basal cytokine production (including IL12, IL-12a); presence of goblet cells (a specialized, mucin-secreting cell of the conjunctiva); ultrastructural features (including tight junctions, desmosomes, apical microvilli) and transepithelial barrier function (as evaluated by measurements of transepithelial electrical resistance (TER) and transepithelial permeability (TER)).

In a further embodiment, the present invention provides an in vitro model of the conjunctival portion of the human ocular surface comprising the cell lines of the present invention. This model can be used to evaluate the conjunctival component of the eye irritation potential of consumer products. This model can be used alone, or to complement testing on human corneal epithelial cells, as part of a test battery that serves as a replacement for the Draize test for the evaluation of the eye irritation potential of some types of products.

The conjunctiva is the primary site for the inflammatory response mounted by the ocular surface. It has vascular and neural components, both of which are likely to be involved in the primary response of the eye to ocular irritants through redness, tearing, chemosis, discharge, stinging, and/or pain.

Barrier function assays, such as transepithelial permeability (TER) and transepithelial electrical resistance (TER) provide a useful criteria for toxicity evaluation. Due to the large surface area of the conjunctiva, particularly compared to the cornea, for example, the ability of a compound to penetrate the conjunctival barrier is an important consideration in the evaluation of its potential toxicity.

Cell viability assays can be used to assess the cytotoxic effects from an-exposure, and compared for utility in this model. The type of cell death, necrosis versus apoptosis, from different treatments can be evaluated. Other potential endpoints include the quantitative determination of effects on expression of proteases, integrins and adhesion molecules, and transcription factors. Different endpoints and methods to measure the effect of potential eye irritants on the ability of the conjunctival cultures to recover (wound healing) may also be evaluated.

Topical treatments may affect mucin expression, and goblet cell density and differentiation. Neural stimulation, like an epithelial debridement wound to the cornea, has been shown to stimulate conjunctival goblet cell mucous secretion, which may be a response to protect the ocular surface. In a co-culture model of conjunctival epithelium and microvasculature, the upregulation of thy-1 on the endothelium by inflammatory cytokines produced by the epithelium is a potential in vitro model for evaluating the angiogenic potential of an exposure.

Potential biological endpoints in the conjunctival 3-D model include perturbations or alterations (morphological, physiological, expression of protein or mRNA) in: barrier function (TER and TER); inflammatory mediator expression (cytokines, chemokines, defensins, lipocalins, arachidonic acid metabolites, PAF, NO, etc.); receptor expression for inflammatory mediators; growth factor or growth factor receptor expression; stress protein expression; angiogenic factor expression (VEGF, angiogenin, FGF, 12-R-HETre, etc.); microvascular permeability (2-R-HETre, etc.); cell viability (cytotoxicity, apoptosis); cellular metabolism (lactate, glucose uptake, LDH etc.); protease or protease inhibitor expression; expression of adhesion molecules and integrins; transcription factor, or other gene expression; cell cycle regulation; cell migration; cell adhesion; cellular differentiation; protein synthesis; ion transport; cytoskeletal protein expression or organization; and cellular morphology, ultrastructure, or histology.

The conjunctival cell lines are preferably cultured on cell culture inserts, where they stratify into multiple cell layers, and form apical tight junctions on the culture inserts. The human bulbar conjunctiva consists of about 4–8 cell layers, depending upon its location in the eye.

The 3-D conjunctival model may be used to evaluate the eye irritation potential of consumer products in a manner similar to the methods described for the use of corneal epithelial cells (See, e.g., Kruszewski et al, 1997; Ward et al, 1997). Preferably, cell lines according to the present invention are grown as a multilayered culture on Cellagen (or other types of) cell culture inserts which provides a 3-D in vitro model of the human conjunctival epithelium. This model is relevant to the tissue of origin because of morphological, ultrastructural, and physiological similarities. Numerous variations are possible, however, including (1) the use of monolayer vs stratified cultures of the human conjunctival cell lines; (2) use of submerged vs airlifted cultures of the human conjunctival cell lines; (3) use of different cell seeding densities on the membranes to obtain different numbers of cell layers and barrier properties; (4) use of different membranes for stratified cultures; and (5) use of new cell lines cloned, or otherwise derived, from HC0597 or HC0708.

In an alternative embodiment of the present invention, a conjunctival cell line according to the present invention may be co-cultured with one or more additional cell types. Such co-cultures provide the opportunity to test a chemical's effect on more than one cell type, in order to more completely determine a chemical's effect on the human eye. Preferred cell types for use in such co-culture models include: corneal epithelial cells; conjunctival keratocytes; endothelial cells and/or microvasculature; mast cells; and Langerhans cells.

Cells in culture according to the present invention may be induced to differentiate; different levels of differentiation may be achieved by growing said cells in different concentrations of calcium, or by the inclusion of different growth factors in the media, or an artificial tear film. In one embodiment, some cells are induced to differentiate into goblet cells.

The following examples are presented in order to more fully illustrate the preferred embodiments of the invention. They should in no way be construed, however, as limiting the broad scope of the invention.

EXAMPLE I

Transfection of Human Conjunctival Cells

Plasmid RSV-T (pRSV-T) is an SV40 ori-construct containing the SV40 early region genes and the Rous sarcoma virus long terminal repeat. The plasmid was amplified and banded twice in cesium chloride (Lofstrand Labs, Gaithersburg, Md.). Primary or secondary cultures ($P_1$ or $P_2$) of human conjunctival epithelial cells were transfected by lipofection, when conjunctival cells were 25–50% confluent. LIPOFECTIN® Reagent (Life Technologies, Gaithersburg, Md.) (30 µl/T-25 flask) was mixed with pRSV-T DNA (10 µg/T-25 flask) in polystyrene tubes. The volume in each polystyrene tube was brought up to 200 µl with serum-free medium and after gentle agitation, the mixture was allowed to incubate at room temperature for 12 minutes. After the incubation period, the medium on the cells was exchanged with 3 ml of serum-free medium per T-25 flask and 1.8 ml serum-free medium was added to each polystyrene tube. Two ml of LIPOFECTIN® Reagent/pRSV-T mixture was slowly added to each T-25 flask of human conjunctival epithelial cells. Control cultures received 30 µl LIPOFECTIN® in 5 ml serum-free medium only. All flasks were incubated at 37° C. with 5% $CO_2$ for 18 hours, at which time the medium was exchanged with fresh serum-free medium. Cultures were fed twice weekly with serum-free medium (KGM) (Clonetics, San Diego, Calif.) and passaged when they were generally 80–90% confluent. Cells were grown in vented tissue culture flasks that were first coated with FNC Coating Mix™ (BRFF, Ijamsville, Md.). The split ratio at each passage was 1:3 or 1:4, depending on how confluent the cultures were when split. Cells were also frozen, in freeze medium containing 90% FBS+10% DMSO, at various passage levels and were stored in liquid nitrogen.

Results

Human conjunctival cell lines produced by transfection are cell lines HC0597 and HC0708. These cell lines were deposited with the American Type Culture Collection (ATCC; 10801 University Blvd., Manassas, Va. 20110-2209) on Mar. 10, 1999, under accession numbers CRL-12658 (HC0597) and CRL-12659 (HC0708).

| Primary cells | Results |
|---|---|
| 5/20/97: 2 T-25 flasks of P1 human conjunctival cells from pooled surgery tissues | cells were passaged at GMEL and transfected at P2; the resulting cell line was designated HC0597 |
| 7/1/97: 3 T-25 flasks of P1 cells from pooled surgeries | cells were passaged at GMEL, but did not survive |
| 7/8/97: 4 T-25 flasks of P1 cells from pooled surgeries | cells were transfected at P1; the resulting cell line was designated HC0708 |

Cell line HC0597 maintained a constant rate of passage and normal appearance for 28 passages, while cell line HC0708 maintained a constant rate of passage and normal appearance for 25 passages. In contrast, primary cultures maintained a constant rate of passage and normal appearance for 5–7 passages. FIG. 1 illustrates the retention of normal epithelial morphology after transfection by cell line HC0597.

EXAMPLE II

Monolayer Cell Culture

T-75 flasks containing cells seeded at $1 \times 10^4$ cells/cm$^2$ and 15 ml serum-free medium (KGM; Clonetics, San Diego, Calif.) were incubated at 37° C. in 5% $CO_2$. Cultures were fed twice weekly with serum-free KGM and passaged when they were generally 80–90% confluent. Cells were grown in vented tissue culture flasks that were first coated with FNC Coating Mix™ (BRFF, Ijamsville, Md.). The split ratio at each passage was 1:3 or 1:4, depending on how confluent the cultures were when split. Cells were frozen in freeze medium containing 90% FBS+10% DMSO at various passage levels and were stored in liquid nitrogen.

Results

Both transfected human conjunctival cell lines demonstrated cobblestone-like morphology typical of epithelial cells.

Both conjunctival cell lines undergo a change in morphology in high-calcium medium (1.15 to 1.8 mM $CaCl_2$). The cells become flattened, and cell—cell junctions become less distinct in high-calcium KGM. These morphological changes are consistent with cells that are becoming more differentiated. Cells can take up to 72 hours to show these changes by light microscopy.

When cultured on FNC-coated glass slides, the conjunctival cell lines grow as a monolayer in low-calcium KGM, but begin to grow on top of each other in high-calcium KGM.

EXAMPLE III

Stratified Cell Culture

Cells were seeded at $1.5 \times 10^5$ cells/14 mm collagen membrane (growth surface=0.64 cm$^2$) (Cellagen™, ICN, Costa Mesa, Calif.). They were then propagated submerged (with medium on the apical surface of the cultures) in low-calcium (0.15 mM $CaCl_2$) serum-free medium for 3 days. Following this, they were grown either submerged or airlifted (without medium on the apical surface of the cultures) in high-calcium (1.15 mM $CaCl_2$) serum-free medium for an additional 3 to 10 days.

Results

Figure 6A:
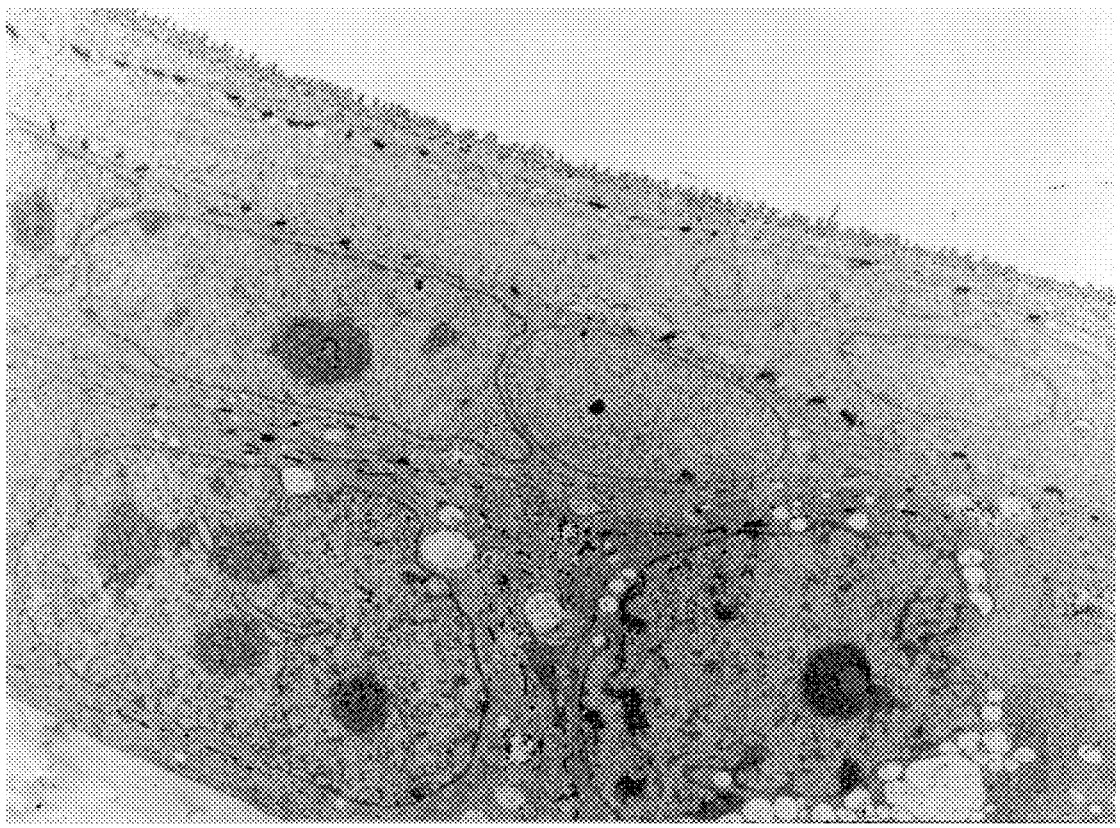
FIG. 6A contains a transmission electron micrograph showing the ultrastructure of cells from a six day submerged culture of HC0708 (P15).
Figure 6B:
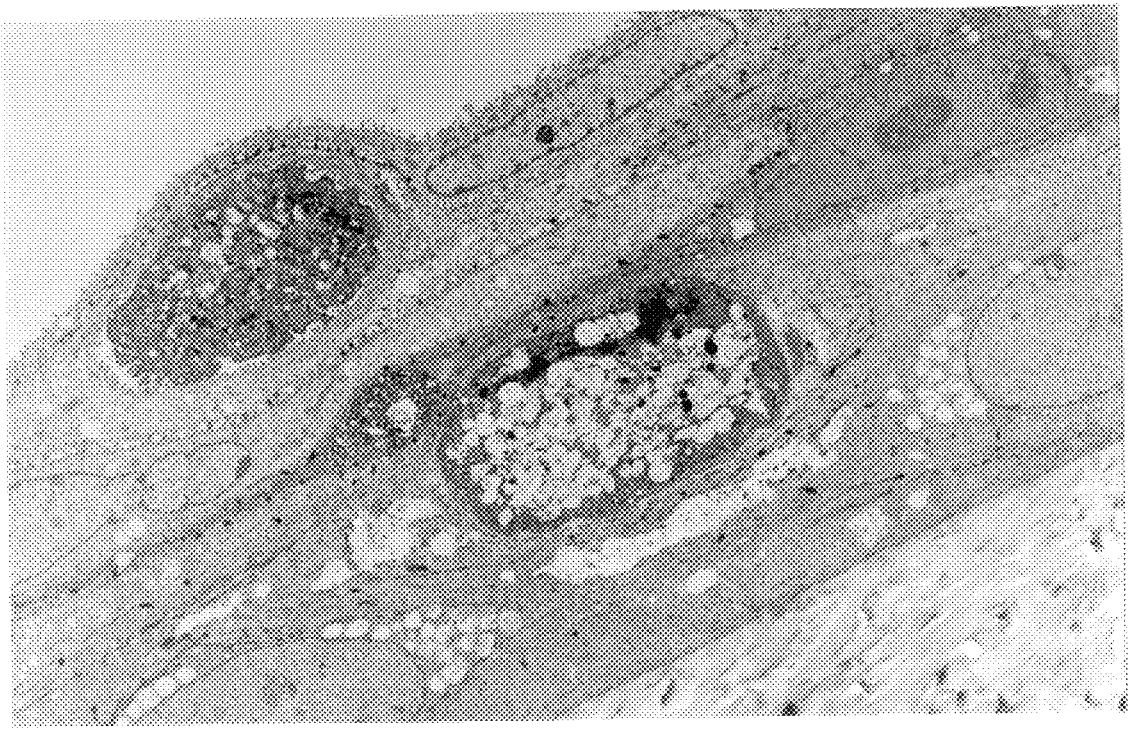
FIG. 6B shows a photomicrograph taken from a six day submerged culture of HC0597 (P14). The cultures stratified into 3–6 cell layers. The stratified HC0708 and HC0597 cultures expressed apical microvilli, numerous desmosomal junctions, tightly packed cells with intercellular interdigitations, and a normal stratification comparable to ocular surface epithelia. Magnification

Both conjunctival cell lines form stratified cultures (multilayers of cells) when grown on permeable membranes in serum-free KGM (see FIGS. 2 and 6).

EXAMPLE IV

Cell Characterization—Growth Characteristics of the Cell Lines

The population doubling times (PDT) and saturation densities (SD) of both conjunctival cell lines were determined at different passage numbers between passage 10 and passage 21–22. The PDT (31.7±0.5 hr) and SD (16.3±0.5× 10$^4$ cells/cm$^2$) for HC0597 remained consistent from P10 through P22. The PDT (30.9±0.4 hr) for HC0708 remained consistent from P10 through P21; the SD (21.5±2.7×10$^4$ cells/cm$^2$) for HC0708 was inconsistent.

SUMMARY OF POPULATION DOUBLING TIME/SATURATION DENSITY EXPERIMENTS USING TRANSFECTED HUMAN CONJUNCTIVAL CELLS.

| | HC0597 | | HC0708 | |
|---|---|---|---|---|
| Passage | PDT (hr.) | S.D. (×10$^4$ cells/cm$^2$) | PDT (hr.) | S.D. (×10$^4$ cells/cm$^2$) |
| 10 | 29.6 | 18.4 | 29.4 | 19.7 |
| 11 | 32.5 | 18.7 | 29.8 | 38.0 |
| 13 | 32.7 | 15.8 | | |
| 14 | 32.8 | 16.2 | 31.7 | 18.4 |
| 15 | | | 31.2 | 27.0 |
| 18 | 30.8 | 15.6 | 32.7 | 16.0 |
| 19 | 32.7 | 15.4 | 29.5 | 18.7 |
| 20 | | | 31.8 | 16.9 |
| 21 | 29.9 | 15.1 | 30.8 | 17.3 |
| 22 | 32.5 | 14.8 | | |

-continued

SUMMARY OF POPULATION DOUBLING TIME/SATURATION DENSITY EXPERIMENTS USING TRANSFECTED HUMAN CONJUNCTIVAL CELLS.

| | HC0597 | | HC0708 | |
|---|---|---|---|---|
| Passage | PDT (hr.) | S.D. ($\times 10^4$ cells/cm$^2$) | PDT (hr.) | S.D. ($\times 10^4$ cells/cm$^2$) |
| Average | 31.7 | 16.3 | 30.9 | 21.5 |
| SEM | 0.5 | 0.5 | 0.4 | 2.7 |

EXAMPLE V

Cell Characterization—Infectious Agent Screening

ViroMed Laboratories, Inc. (Minneapolis, Minn.) screened HC0597 (P14) and HC0708 (P10) for the presence of seven human viruses by PCR assays. Both cell lines were found to be free of viral DNA for: hepatitis B, hepatitis C, HIV-1, HIV-2, HTLV-I/II, and cytomegalovirus.

HC0597 (P14) and HC0708 (P10) were screened for the presence of mycoplasma by Bionique Testing Laboratories, Inc. (Saranac Lake, N.Y.) using a test known as the fluorochrome DNA stain. Both cell lines were found to be negative for mycoplasma.

EXAMPLE VI

Cell Characterization—Immunofluorescence Assays

HC0597 and HC0708 cells at P10–P20 were cultured as monolayers on FNC coated glass slides (3×14 mm wells per slide) for one day in low calcium (0.15 mM CaCl$_2$) medium and then either 3 days more in low calcium or 3 days in high calcium (1.15 or 1.65 mM CaCl$_2$) medium. Prior to staining, the medium was aspirated, and the slides were rinsed in PBS and fixed in ice cold acetone:methanol (1:1) for 10 minutes. After rehydration in PBS, the slides were stored refrigerated in PBS until used.

For the assays, slides were removed from storage, overlaid with 600 µl of appropriately diluted primary antibody per slide, and incubated for 30 minutes at room temperature in a humidified chamber. Mouse IgG$_1$ and PBS were used as two negative control primary antibodies. After 2 washes in PBS and 1 wash in PBS+0.05% Tween 20, slides were overlaid with 600 µl of appropriately diluted FITC-labeled Goat anti-mouse second antibody per slide, and incubated for 30 minutes at room temperature, in a humidified chamber. An appropriately diluted FITC-labeled Goat IgG was utilized as a negative control second antibody that was tested for each primary antibody. After washing four times with PBS, coverslips were mounted with mounting medium on each slide and sealed with clear nail polish to preserve the slide for photomicroscopy.

Cells were viewed with a Zeiss epifluorescence microscope (Model ICM 405, 100 watt light source), using a 10× objective with either a 25× or a 40× lens and fluorescein filters. Fluorescent photomicrographs were prepared using Kodak Elite Chrome slide film (100 ASA) with a 30-second exposure time.

Results:

For both cell lines, HC0597 and HC0708 immunostaining with the anti-keratin antibodies AE1, AE3 and M6B10 (anti-keratin 4) was positive. All controls were negative. AE1 is an antibody that recognizes most of the acidic keratins, AE3 is an antibody that recognizes all of the known basic keratins, and keratin 4 (K4) is a keratin preferentially expressed in differentiated conjunctival cells. The staining with AE1 and AE3 was positive for ~100% of the cells while the staining pattern for K4 was patchy.

An experiment was performed to evaluate the expression of K4 as a marker for more differentiated conjunctival epithelial cells. Anti-K4 reacted with small "islands" of cells or with individual cells when the HC0597 cells were cultured on glass slides in high and low calcium KGM, respectively (see FIG. 3). Anti-K4 reacted with small "islands" and single cells or with no cells when the HC0708 cells were cultured on glass slides in high and low calcium KGM, respectively. HC0597 cells in high-calcium had a more dense population of K4-positive cells than did HC0708 cells. Cells that were cultured in high-calcium medium had areas where the cells appeared to be growing on top of each; these "stratified" cells were the K4-positive regions of the cultures. Cells that were cultured in low-calcium medium remained monolayer in appearance, and only scattered individual cells were K4-positive. These results support the conclusions that: 1) K4 is expressed to a greater extent in more differentiated cells, and 2) that the HC0597 cell line can differentiate to a greater extent than the HC0708 cell line. The fact that the HC0597 cell line forms "better" tight junctions than the HC0708 cell line also supports these conclusions. The corneal epithelium is reported to express some K4, but less than the conjunctiva.

Since the transfection process used the SV40 large T antigen plasmid RSV-T, anti-SV40 T-Ag (Antibody 2) was used to determine whether or not the large T antigen (T-Ag) from the RSV-T plasmid had been incorporated into the DNA of the cells. The cell lines stained positive for the presence of T-Ag. This, in addition to the fact that the cell lines lived longer than the non-transfected control cells, shows that the cell lines were transfected and have incorporated the plasmid DNA into their own DNA.

EXAMPLE VII

Cell Line Characterization—Karyotype and Isozyme Analysis

Cell lines HC0597 (P10) and HC0708 (P11) were sent to Children's Hospital of Michigan for these analyses. In each line, chromosomes in 100 metaphases were counted for ploidy distribution and exact chromosome counts were done for 30 metaphases. HC0597 is an aneuploid human female (XX) with most chromosome counts in the hypotetraploid range. HC0708 is a hypotetraploid human female (XXX/XXXX). About 10% of the observed metaphases from this line are of male origin in essentially a female cell line. The marker chromosomes for each cell line are different, but both show involvement of chromosomes 2 and 16.

The isoenzyme phenotype is the same for both HC0597 and HC0708 and no multiple bands were observed in any of the enzymes signifying the purity of each cell line (i.e., lack of contamination by another cell type). The phenotypic frequency of the phenotype was calculated to be 0.0703. This indicates that less than 8% of any human cell lines might be expected to have an isozyme phenotypic profile identical to this. All cells from both lines reacted with fluorescein-conjugated anti-human antiserum, and none reacted with fluorescein-conjugated anti-mouse antiserum.

EXAMPLE VIII

Cell Characterization—Presence of Goblet Cells as Detected by Periodic Acid-Schiff (PAS) Staining HC0597 and HC0708 cells were cultured as monolayers on FNC coated glass slides for one day in low-calcium (0.15 mM CaCl$_2$) medium and then either 3 days more in low-calcium or 3 days in high-calcium (165 mM CaCl$_2$) medium. Prior to staining, the slides were rinsed in PBS and fixed in 10% neutral buffered formalin with 0.55 cetylpyridinium chloride for 30 minutes at room temperature. Two forms of PAS staining were performed: 1) PAS counter-stained with hematoxylin (PAS-hematoxylin) and 2) Alcianblue-PAS.

For PAS-hematoxylin staining, fixed slides were rinsed for 1 minute in running tap water. The slides were then immersed in periodic acid solution for 5 minutes at room temperature and rinsed in several changes of distilled water. Slides were then immersed in Schiff's Reagent for 15 minutes at room temperature, followed by washing for 5 minutes in running tap water. The slides were then counter-stained for 90 seconds in hematoxylin solution and again rinsed for 15–30 seconds in running tap water. Following air drying, the slides had coverslips mounted on them using Permount, and were observed under the microscope.

For Alcian blue-PAS staining, the fixed slides were briefly dipped in 3% acetic acid and stained with 0.5% alcian blue in 3% acetic acid for 30–45 minutes at room temperature. The slides were then rinsed in running tap water for 1 minute, immersed in periodic acid solution for 5 minutes at room temperature and rinsed in several changes of distilled water. Slides were then immersed in Schiff's Rreagent for 15 minutes at room temperature, followed by washing for 5 minutes in running tap water. Following air drying, the slides had coverslips mounted on them using Permount, and were observed under the microscope.

Results

The PAS-hematoxylin staining method showed the presence of bright pink/magenta (positive) stained cytoplasm of some single cells and very small groups of cells in the low-calcium medium (see FIG. 5A). In the high-calcium medium, larger clumps of cells were stained.

The Alcian blue-PAS staining method showed the presence of bright pink/magenta (positive) stained cells among lighter pink and unstained areas of cells (see FIG. 5B). Once again, the cells grown in low-calcium showed single cells and very small groups of stained cells, whereas the cells grown in high-calcium showed large clumps of brightly stained cells.

In general, both staining methods showed the presence of goblet cells, with the cells grown in high-calcium having a greater number of positively stained cells.

Additionally, both of these conjunctival cell lines express mRNA for the goblet cell specific mucin MUC5ac (Jumblatt et al., 1999). The tear film mucin MUC5ac is produced by conjunctival goblet cells. This also supports our identification, by PAS staining, of goblet cells in the cell lines.

EXAMPLE IX

Expression of Inflammatory Mediators Characteristic of Conjunctival Epithelial Cells— Basal Cytokine and ICAM-1 Production The baseline secretion of a defined set of cytokines (IL-1α, IL-1ra, IL-6, IL-8, TNF-α, GM-CSF), that were previously reported to be produced by human conjunctival epithelial ells (Gamache et al., 1997), was determined in HC0597 and HC0708 culture media. In addition, secreted and cell-bound forms of the adhesion molecule ICAM-1 were quantitated.

IL-1α, IL-1ra, IL-6, IL-8, TNF-α, GM-CSF, and s-ICAM-1 levels in 24 hr culture media were measured using ELISA Immunoassay Kits (R&D Systems, Inc., Minneapolis, Minn.). KGM (4 ml/T-25 flask), with and without hydrocortisone (HC) was incubated with 90% confluent cell cultures for 24 hr. Media was removed, centrifuged to remove cell debris, and stored in aliquots at −70° C. in siliconized eppendorf tubes. The cells were rinsed with PBS, and solubilized with a 5 min. incubation in 0.1N NaOH. Protein in the solubilized cells was determined with the BioRad DC Protein Assay Kit. Cell-bound ICAM-1 was measured using the previously described assay (Trocme et al., 1998).

Results

For the inflammatory mediators that have been evaluated, the conjunctival cell lines HC0597 and HC0708 express the same inflammatory mediators that are produced by primary cultures of human conjunctival epithelial cells.

HC0597 and HC0708 produced small amounts of IL-1α, IL-1ra, IL-6, IL-8, TNF-α and GM-CSF. In general, cells incubated in media (KGM) without hydrocortisone produced more of the cytokines.

HC0597 and HC0708 produced small amounts of the cell-bound adhesion molecule ICAM-1, and undetectable amounts of s-ICAM-1. Human conjunctival epithelial cells were previously reported to express the ICAM-1 adhesion molecule, which is an important component of the inflammatory cascade.

EXAMPLE X

3-D Model Development—Seeding Cellagen Inserts with Different Numbers of Cells and in Media with Different Concentrations of Calcium Transepithelial electrical resistance (TER) measurements were made at room temperature using an Endohm™-12 attached to an Epithelial Volt Ohmmeter (EVOM™) (World Precision Instruments, Sarasota, Fla.). The Endohm™-12 contained 3 ml PBS and the cultures contained 200 μl PBS, with readings being taken after 20 seconds. Background readings from empty inserts were subtracted from all readings. The resulting numbers were multiplied by 0.64 cm$^2$ to obtain the Resistance (ohms cm$^2$).

Results

The effect of seeding the collagen membranes with different numbers of HC0597 cells was evaluated. The standard seeding density of 1.5×10$^5$ cells was compared to seeding three-fold more or less cells. Seeding more or less cells did not significantly alter the TER. Seeding 1.5×10$^5$ cells per collagen membrane provided a good TER that was stable over the 6 to 11 days of culture. 1.5×10$^5$ cells per membrane is the preferred seeding density.

The effect of maintaining the HC0597 cells in media (KGM) containing different concentrations of calcium was determined (FIG. 4). Stratified cultures prepared as described in Example II were used in these studies. After the initial three days of growth the cultures were transferred to KGM containing 0.15, 1.15, 1.5 or 1.8 mM CaCl$_2$. The cultures were maintained by daily feeding with KGM containing these concentrations of calcium until the TER was measured on day 6, 9, or 11. Results indicate that maximal TER is attained with any of these calcium concentrations, and is maintained over the 6–11 days of culture.

The effect of the media components, serum and retinoic acid, on the TER were evaluated. Maintenance of the HC0597 cultures in KGM containing 10% serum for 6 days did not affect the TER. Maintenance of the HC0597 cultures in KGM containing 10$^{-6}$M retinoic acid for 6 days significantly decreased the TER.

EXAMPLE XI

3-D Model Characterization—Barrier Function Assays (Transepithelial Permeability and Transepithelial Electrical Resistance)

Stratified cultures, prepared as described in Example III, were used in these studies. Transepithelial permeability (TER) measurements were made on submerged cultures on days 3 & 6 and airlifted cultures on days 6, 10, and 13 of growth. Briefly, 200 µl of sterile sodium fluorescein (0.02% w/v) was added to the apical surface of the cultures and incubated with 1 ml KGM in the basal compartment for 30 minutes at 37° C. with 5% $CO_2$. Following incubation, 200 µl of the basal media was read at 490 nm in a 96-well plate reader (Dynatech, Chantilly, Va.).

Transepithelial electrical resistance (TER) measurements were made on submerged cultures on days 3 & 6 and airlifted cultures on days 6, 10, and 13 of growth.

Results

Both cell lines demonstrated a similar ability to retain fluorescein at the apical surface (baseline TER). Both submerged and airlifted cultures demonstrated similar fluorescein retention: for airlifted, day 10 cultures (3 days submerged then 7 days airlifted) TER was 98±1% for HC0597 and was 96±1% for HC0708; for submerged, day 6 cultures (6 days submerged) TER was 99±0% for HC0597 and was 97±1% for HC0708.

Maximum TER was reached in airlifted cultures at day 10 for both cell lines: 364±42 ohms×cm$^2$ for HC0507 and 217±20 ohms×cm$^2$ for HC0708. Submerged cultures reached a maximum TER by day 6: 319±45 ohms×cm$^2$ for HC0597 and 182±11 ohms×cm$^2$ for HC0708. Data generated subsequent to these early experiments indicate that stratified cultures of the HC0597 cell line can routinely attain a transepithelial electrical resistance (TER) of 400–600 ohms×cm$^2$.

EXAMPLE XII

3-D Model Characterization—Transmission Electron Microscopy (TEM)±Mucin Layer Stratified cultures, prepared as described in Example III, were fixed for TEM by incubating the cultures in sodium cacodylate buffer (0.1M) containing 2.5% glutaraldehyde for 60 minutes at room temperature. The addition of 0.5% cetylpyridinium chloride (CPC) to this fixative solution was used to preserve the mucin layer. Cultures were then stored at 4° until processed.

Results

Six day submerged cultures of HC0597 (P14) and HC0708 (P15) stratified into 3–6 cell layers and expressed apical microvilli, tight junctions, and intracellular adhesions (see FIG. 6). Ten day airlifted cultures (3 days submerged, then 7 days at the air-liquid interface) of HC0597 (P14) and HC0708 (P15) stratified into 6–8 cell layers. Typically there were 2–3 layers of squamous apical cells, and occasional dead surface cells on the airlifted cultures.

An apical mucin layer was produced by the airlifted cultures (see FIG. 14). The mucin layer was more frequently found between surface cell layers, as well as in an apical layer, in submerged cultures. These results demonstrate ultrastructural features characteristic of the conjunctiva. The stratification and ultrastructure of the submerged cultures is best representative of the bulbar conjunctival epithelium. The photomicrographs of HC0597 and HC0708 (see FIG. 6) show features illustrated in published photomicrographs of the in vivo tissue, including: apical microvilli, numerous interdigitations, abundant mitochondria and endoplasic reticulum, intermediate filaments, desmosomal junctions, and tight junctions. The TEM photomicrographs also indicate the presence of goblet cells containing multiple secretory vacuoles.

EXAMPLE XIII

3-D Model Characterization—Topical Treatment with Chemicals and Products

Stratified cultures as described above are used. Cultures are re-fed with high-calcium KGM the day before treatment. Immediately before use, test materials are diluted to the appropriate concentrations using high-calcium KGM. Cultures are typically treated on days 6–10 of growth. High-calcium KGM is used as a negative control. Using a positive displacement pipette, a small volume (typically about 100 µl) of each dilution of test material or control is added to the apical surface of each culture. When the cultures are grown submerged, the apical medium must be removed prior to the addition of test material. The treated cultures are incubated at 37° C. with 5% $CO_2$ in a humidified incubator. The total exposure time to the test material is 5 minutes but could be changed, especially if a time-course is being tested as opposed to the dose-response, which is done at a fixed time. After exposure, the test material and medium are aspirated from the cultures and the cultures are rinsed three times without letting the cells dry out. The cultures are then used for whatever endpoint is being evaluated.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for producing a human conjunctival epithelial cell line with an extended lifespan, comprising:
   (a) culturing human conjunctival epithelial cells in serum-free medium;
   (b) transfecting said cells with a vector capable of transfecting said conjunctival epithelial cells such that said cells become continuously growing and retain their phenotypic characteristics, including stratification and transepithelial barrier function; and
   (c) recovering said continuously growing conjunctival epithelial cells.

2. The method of claim 1, wherein said vector is a large T antigen plasmid.

3. The method of claim 2, wherein said plasmid is pRSV-T.

4. An human conjunctival epithelial cell line with extended lifespan produced by the method of claim 1.

5. A method for determining the effect of a chemical or drug on the human eye comprising:
   (a) contacting a human conjunctival epithelial cell line produced by the method of claim 1 with said chemical or drug; and
   (b) determining the effect of said chemical or drug on said cell culture.

6. Human conjunctival epithelial cell line HC0597.

7. Human conjunctival epithelial cell line HC0708.

8. A human conjunctival cell line with extended lifespan, wherein said human conjunctival epithelial cell line is a clone, derivative, mutant, or transfectant of the cell line HC0597 of claim 6, wherein the cells of said cell line, when cultured, grow continuously and retain the phenotypic characteristics of conjunctival epithelial cells, including stratification and transepithelial barrier function.

9. A human conjunctival cell line with extended lifespan, wherein said human conjunctival epithelial cell line is a clone, derivative, mutant, or transfectant of the cell line HC0708 of claim 7, wherein the cells of said cell line, when cultured, grow continuously and retain the phenotypic characteristics of conjunctival epithelial cells, including stratification and transepithelial barrier function.

* * * * *